(12) United States Patent
Lehmann et al.

(10) Patent No.: US 9,872,674 B2
(45) Date of Patent: Jan. 23, 2018

(54) ENTRAPMENT AND CONTAINMENT SYSTEM FOR USE WITH A MORCELLATOR AND METHOD OF ENTRAPPING AND CONTAINING MATERIAL PRODUCED DURING MORCELLATION PROCEDURE

(71) Applicant: Boehringer Laboratories Inc., Phoenixville, PA (US)

(72) Inventors: Allison Lloyd Lehmann, Norristown, PA (US); Christopher L. Radl, Malvern, PA (US); Trevor Smith, Phoenixville, PA (US); Michael Reed Vennel, Philadelphia, PA (US)

(73) Assignee: Boehringer Laboratories Inc., Phoenixville, PA (US)

( * ) Notice: Subject to any disclaimer, the term of this patent is extended or adjusted under 35 U.S.C. 154(b) by 248 days.

(21) Appl. No.: 14/680,693

(22) Filed: Apr. 7, 2015

(65) Prior Publication Data
US 2015/0320409 A1 Nov. 12, 2015

Related U.S. Application Data

(60) Provisional application No. 61/989,911, filed on May 7, 2014, provisional application No. 62/117,755, filed on Feb. 18, 2015.

(51) Int. Cl.
| *A61B 17/00* | (2006.01) |
|---|---|
| *A61B 1/313* | (2006.01) |
| *A61B 17/221* | (2006.01) |
| *A61B 1/04* | (2006.01) |
| *A61B 17/32* | (2006.01) |

(52) U.S. Cl.
CPC .......... *A61B 17/00234* (2013.01); *A61B 1/04* (2013.01); *A61B 1/3132* (2013.01); *A61B 17/221* (2013.01); *A61B 2017/00287* (2013.01); *A61B 2017/00296* (2013.01);
(Continued)

(58) Field of Classification Search
CPC ........................................... A61B 2017/00287
See application file for complete search history.

(56) References Cited

U.S. PATENT DOCUMENTS

| 5,037,379 A | * | 8/1991 | Clayman | .......... | A61B 17/00234 |
|---|---|---|---|---|---|
| | | | | | 128/849 |
| 5,176,687 A | * | 1/1993 | Hasson | ............ | A61B 17/00234 |
| | | | | | 606/114 |

(Continued)

*Primary Examiner* — Shaun L David
(74) *Attorney, Agent, or Firm* — Caesar Rivise, PC (57) ABSTRACT

Entrapment and collection systems and method of entrapping and collecting biologic material produced on a patient are disclosed. The systems include a collection bag which formed of a flexible sheet material having a hollow interior, a first mouth and a second mouth. The first mouth is openable to enable the biological structure to be disposed in the hollow interior and to enable a removal instrument, e.g., a morcellator, to be introduced therethrough to engage the biologic structure to effect a procedure on it. The second mouth enables a viewing instrument to be extended through it for visualizing the procedure and is closeable by a drawstring to entrap biologic material produced by the procedure after the removal instrument and viewing instrument have been removed, whereupon the collection bag may be withdrawn from the body of the patient.

12 Claims, 6 Drawing Sheets

(52) U.S. Cl.
CPC .............. *A61B 2017/00557* (2013.01); *A61B 2017/2212* (2013.01); *A61B 2017/320024* (2013.01)

(56) References Cited

U.S. PATENT DOCUMENTS

| | | | | |
|---|---|---|---|---|
| 5,368,597 A * | 11/1994 | Pagedas | ............ | A61B 17/00234 600/37 |
| 5,480,404 A * | 1/1996 | Kammerer | ....... | A61B 17/00234 606/113 |
| 5,611,803 A * | 3/1997 | Heaven | ............ | A61B 17/00234 606/110 |
| 5,618,296 A * | 4/1997 | Sorensen | ......... | A61B 17/32002 606/167 |
| 5,853,374 A * | 12/1998 | Hart | ................. | A61B 17/00234 600/562 |
| 6,270,505 B1 * | 8/2001 | Yoshida | ............ | A61B 17/00234 606/127 |
| 6,350,267 B1 * | 2/2002 | Stefanchik | ....... | A61B 17/00234 606/114 |
| 2003/0216611 A1 * | 11/2003 | Q. Vu | .............. | A61B 17/00234 600/37 |
| 2004/0138587 A1 * | 7/2004 | Lyons, IV | ........ | A61B 17/00234 600/562 |
| 2007/0135780 A1 * | 6/2007 | Pagedas | ............ | A61B 17/00234 604/327 |
| 2008/0033451 A1 * | 2/2008 | Rieber | ............ | A61B 17/00234 606/114 |
| 2009/0043315 A1 * | 2/2009 | Moon | ............ | A61B 17/00234 606/114 |
| 2010/0219090 A1 * | 9/2010 | Thatcher | ................ | A45C 11/38 206/316.1 |
| 2012/0109144 A1 * | 5/2012 | Chin | ...................... | A61B 17/00 606/114 |
| 2013/0184536 A1 * | 7/2013 | Shibley | ............ | A61B 17/00234 600/235 |
| 2014/0155698 A1 * | 6/2014 | Seo | .................... | A61B 17/3423 600/204 |
| 2014/0236110 A1 * | 8/2014 | Taylor | ............ | A61B 17/00234 604/327 |
| 2014/0236168 A1 * | 8/2014 | Shibley | ............... | A61M 13/003 606/114 |
| 2014/0330285 A1 * | 11/2014 | Rosenblatt | ............. | A61B 17/42 606/114 |
| 2015/0105755 A1 * | 4/2015 | Lovell | ............ | A61B 17/3205 604/543 |
| 2015/0297254 A1 * | 10/2015 | Sullivan | ........... | A61B 17/32002 606/114 |
| 2015/0305728 A1 * | 10/2015 | Taylor | ............. | A61B 17/00234 606/114 |
| 2015/0305772 A1 * | 10/2015 | McCauley | ......... | A61B 17/3423 606/114 |
| 2016/0135798 A1 * | 5/2016 | MacLeod | ......... | A61B 17/00234 606/114 |

* cited by examiner

ENTRAPMENT AND CONTAINMENT SYSTEM FOR USE WITH A MORCELLATOR AND METHOD OF ENTRAPPING AND CONTAINING MATERIAL PRODUCED DURING MORCELLATION PROCEDURE

CROSS-REFERENCE TO RELATED APPLICATIONS

This utility application claims the benefit under 35 U.S.C. §119(e) of Provisional Application Ser. No. 61/989,911 filed on May 7, 2014, entitled Entrapment System For Use With a Morcellator and Method of Entrapping Material Produced During Morcellation Procedure and Provisional Application Ser. No. 62/117,755, filed on Feb. 18, 2015, entitled Containment System For Use With Morcellator and Method of Entrapping Material Produced During Morcellation. The entire disclosures of these provisional applications are incorporated by reference herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

FIELD OF THE INVENTION

The disclosed invention relates to medical containment devices and more particularly to devices and methods of use for entrapping materials produced during a morcellation procedure on a patient.

BACKGROUND OF THE INVENTION

More and more medical procedures for removing a mass of tissue or an organ from the abdomen of a patient are accomplished laparoscopically using a morcellator. Morcellators are surgical instruments which typically take the form of a hollow cylinder that penetrates the abdominal wall and has a free distal end in the form of a high speed moving cutter or blade. Many morcellators include a central lumen or passageway through which a grasping instrument can be inserted to pull the mass to be removed into a rotating cutter or blade to sever an extractable piece of that mass, which is withdrawn out of the morcellator through its central passageway.

While morcellators are effective for removing tissue from the body of the patient, the high-speed cutting action may free up some cells or other biological material, which can be dispersed within the peritoneal cavity. Thus, for example, if the tissue being removed is not known to be cancerous, but is in fact cancerous, there could be a release of cancer cells throughout the peritoneal cavity and from there elsewhere. Hence, it is possible for the process of morcellation to have an adverse effect on the patient, e.g., convert an undiagnosed stage II cancer into a stage IV cancer.

Accordingly, a need exists for a system for effectively and efficiently entrapping cells and other biological material produced during morcellation, yet which does not interfere or otherwise detract from the efficiency of a morcellation procedure and which can be used with conventional morcellators and laparoscopes. The subject invention addresses that need.

SUMMARY OF THE INVENTION

One aspect of this invention is a collection bag which may be part of a system for use in a procedure, e.g., morcellation, on a biologic structure in a cavity in a patient to entrap biologic material produced by the procedure. The bag is configured to be introduced through a port into the patient and comprises a body formed of a flexible sheet material and has a hollow interior. The body has a top portion including a first mouth located thereat and a second portion projecting outward from the body. The second portion has a second mouth thereat. The first mouth is openable to enable the biological structure to be introduced therethrough into the hollow interior and to enable an instrument to be introduced therethrough to engage the biologic structure to effect a procedure on the biologic structure. The second mouth is openable to enable a viewing instrument to be extended therethrough into the hollow interior to enable the visualization of the engagement of the biologic structure by the instrument. The second mouth is closeable to entrap biologic material produced by the procedure, whereupon the collection bag may be withdrawn from the body of the patient through the port.

In accordance with one preferred aspect of the invention the collection bag comprises a draw-string coupled to the second portion of the collection bag and which is extendable through the port to draw the second portion of the collection bag toward the port during the withdrawal of the collection bag from the body of the patient. Moreover, the port comprises a first port and the first mouth comprises a pair tabs. One of the pair of tabs of the first mouth comprises a first edge portion of the first mouth and the other of the pair of tabs of the first mouth comprises a second edge portion of the first mouth. The second edge portion of the first mouth is laterally off-set from the first edge portion of the first mouth. In addition, the second mouth comprises a pair of tabs, one of the pair of tabs of the second mouth comprises a first edge portion of the second mouth and the other of the pair of tabs of the second mouth comprises a second edge portion of the second mouth. The second edge portion of the second mouth is laterally off-set from the first edge portion of the second mouth. The first mouth is openable by grasping at least one of the pair of tabs of the first mouth to enable the biological structure to be introduced therethrough.

In accordance with another preferred aspect of this invention the collection bag forms a part of a system, with the system additionally comprising a tubing assembly. The tubing assembly is configured for delivering a first pressurized gas through a first conduit into the hollow interior of the collection bag and for delivering a second pressurized gas through the second conduit into the cavity in the patient and outside of the collection bag, with the pressure of the second pressurized gas being slightly less than the pressure of the first pressurized gas so that the collection bag is inflated within the cavity of the patient.

Another aspect of this invention constitutes a method for removing a biologic structure within a cavity in the body of a patient and for entrapping biologic material produced by the removal of the biologic structure. The method basically entails providing a collection bag having a body formed of a flexible sheet material. The bag has a hollow interior, a first mouth in communication with the hollow interior and a second mouth in communication with the hollow interior.

The first mouth is openable, as is the second mouth. The collection bag is introduced through a first port into a cavity in the patient with the second mouth extending from the cavity out of a second port in the patient. The first mouth is opened to enable the biological structure to be introduced therethrough into the hollow interior of the bag. A viewing instrument is introduced through the second mouth into the hollow interior of the bag. A removal instrument, e.g., a morcellator, is introduced through the first mouth to engage the biologic structure to effect a procedure on it. The procedure is visualized by the viewing instrument. The removal instrument and the viewing instrument are removed from the collection bag and the second mouth of the bag is closed to entrap biologic material produced by the procedure, whereupon the bag is withdrawn from the body of the patient through the port.

In accordance with one preferred aspect of the method of this invention the cavity comprises the peritoneal space and wherein the method additionally comprises providing a first pressurized gas at a first pressure into the hollow interior of the collection bag within the peritoneal space to inflate the collection bag. A second pressurized gas may be provided into the peritoneal space, with the second pressurized gas being at a second pressure that is slightly less than the first pressure, whereupon the collection bag is inflated within the peritoneal space.

In accordance with another preferred aspect of the method of this invention the biologic structure comprises a fibroid tumor or the uterus.

DETAILED DESCRIPTION OF THE PREFERRED EMBODIMENTS

Figures 1, 2:
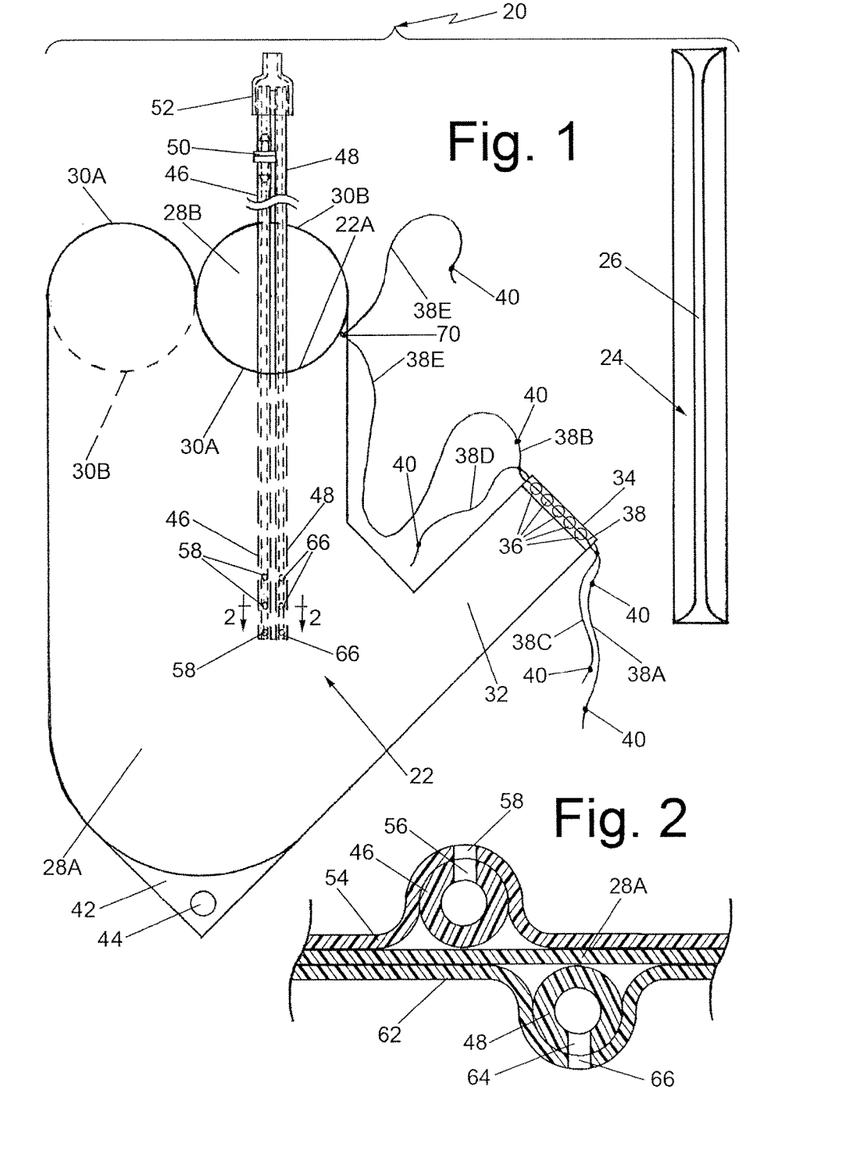
FIG. 1 is a plan view of one exemplary embodiment of an entrapment system constructed in accordance with this invention, with the system comprising a collection bag and an introducer.
FIG. 2 is a greatly enlarged sectional view taken along line 2-2 of FIG. 1.

Referring now to the drawings wherein like characters refer to like parts there is shown one exemplary embodiment of an entrapment system 20 constructed in accordance with this invention for use with a conventional morcellator and a conventional laparoscope to effect the removal of a specimen e.g., a fibroid tumor, from an insufflated region, e.g., the peritoneal cavity, of a patient during a laparoscopic procedure. The system 20 basically comprises a collection bag 22 and an introducer 24. The introducer is arranged to hold the collection bag therein to introduce it into the insufflated region of the patient's body. It basically comprises a tubular member formed of any suitable material, e.g., Polyethylene terephthalate. The introducer has a longitudinal slot 26 extending the length thereof, with each end of the slot being rounded. The introducer has a length of approximately 15 cm, an inside diameter of approximately 1.25 cm, and a wall thickness of approximately 0.5 mm. Those dimensions are merely exemplary.

The collection bag basically comprises a hollow body formed of two sheets or panels 28A and 28B of any suitable flexible material, e.g., polyurethane of any suitable thickness, e.g., 0.002 to 0.020 inches. The sheets overlie each other and together have a profile somewhat like a mitt, as best seen in FIG. 1. Moreover, as can be clearly seen in that figure, the upper sheet 28A includes an undulating S-shaped edge 30A, while the upper edge of the lower sheet 28B has an undulating S-shaped edge 30B. The undulations of the S-shaped edges are offset from each other so that the left side of the edge 30A projects beyond the left side of the edge 30B, while the right side of the edge 30B extends beyond the right side of the edge 30A. The portions of the sheets 28A and 28B contiguous with the edges 30A and 30B are unsealed, i.e., not connected to each other, to form the mouth 22A of the collection bag 22. The offset nature of the edges of the mouth of the bag facilitate the opening of the bag, given the nature of the fact that the bag is formed of two thin sheets of material which may tend to stick together, since the edges provide easily graspable portions of each sheet that can be grasped to open the mouth of the bag.

Being of somewhat mitt-like in shape the bag includes an angularly projecting portion or arm 32, with the portions of the upper and lower panels 28A and 28B sealed to each other along the periphery of the arm 32 except for the free end 34 which forms the mouth of the arm. The material of each of the sheets 28A and 28B at the free end of the arm is folded over itself to form a channel or passageway through which a portion of a flexible drawstring 38 extends. The drawstring extending through the channel forms a purse string mouth or closure, which can be sealed closed by pulling on the ends of the drawstring (as will be described later). In order to enable the material making up the mouth to gather itself easily and collapse to be completely sealed closed when drawstring is pulled, the material of the panels 28A and 28B includes a series of spaced apertures 36 in the material forming the channel through which the drawstring extends. This renders the mouth of the arm more "gatherable" than if no such apertures were used. The drawstring is arranged to open and close the mouth 34 of the arm. To that end, the drawstring includes several segments, 38A, 38B, 38C, 38D, and 38E. The drawstring segments are connected and arranged such that pulling outward on the segments 38A and 38B closes the mouth 34, while pulling outward on the drawstrings 38C and 38D opens the mouth 34. The segment 38E is connected to segment 38B and extends through an opening 70 in the panels 28A and 28B adjacent the bag's mouth 22A to facilitate the removal of the collection bag from the peritoneal cavity after the bag has been used to morcellate the specimen within it (as will be described in detail later). The various segments of the drawstring 38 include knots 40 strategically located to hold the drawstring in place on the collection bag and ensure proper operation, e.g., they act as stops to prevent over-extension of the drawstring when a segment is pulled.

The bottom portion of the panels 28A and 28B are sealed together to form a tab 42 having an opening 44 therein. The tab and its opening are provided to enable a grasper instrument to grasp the bag at the tab/opening to help pull the bag into the peritoneal cavity during the bag's deployment (which will also be described in detail later).

The collection bag 22 also includes a tube assembly which is provided to effect the inflation of the bag once it has been deployed within an insufflated peritoneal cavity. As best seen in FIGS. 1 and 2, the tube assembly basically comprises a pair of flexible tubes 46 and 48, a check valve 50 and a Y-connector 52. The tube 46 is disposed under a strip 54 (FIG. 2) of flexible sheet material secured to the outer surface of the top panel 28A of the collection bag and extends from approximately the middle of the bag for some distance, e.g., 10 cm, beyond the mouth of the bag. The material forming the strip 54 is the same material as that forming the panels 28A and 28B. The tube 46 includes a series of three apertures 56 located at the distal end of the tube. Those apertures are aligned with a similar series of apertures 58 in the strip 54. Thus, the interior of the tube 46 is in fluid communication with the outside of the collection bag. The proximal end of the tube 46 is connected to one side of the check valve 50. The other side of the check valve 50 is connected to another segment of the tube 46, which is connected to one leg of the Y-connector 52. The check valve is of any suitable construction and has a cracking pressure of a couple of mm of Hg such that the pressure within the peritoneal cavity is a couple of mm Hg lower than the pressure of the gas coming directly from the insufflator. The tube 48 is disposed under a strip 62 of flexible sheet material secured to the inner surface of the top panel 28A of the collection bag and extends from approximately the middle of the bag for some distance, e.g., 10 cm, beyond the mouth of the bag. The material forming the strip 62 is the same material as that forming the panels 28A and 28B. The tube 48 includes a series of three apertures 64 located at the distal end of the tube. Those apertures are aligned with a similar series of apertures 66 in the strip 62. Thus, the interior of the tube 48 is in fluid communication with the inside of the collection bag 22. The proximal end of the tube 48 is connected to another leg of the Y-connector 52. The common leg of the Y-connector is arranged to be secured to a conduit 68 from an insufflator. By virtue of the check valve 50 the pressure delivered to the peritoneal cavity is lower than the pressure delivered within the bag. Thereby enabling the bag to distend and remain distended.

In an alternate embodiment (not shown), the tube assembly may be separate from the bag. In such a case, after the bag is installed within the patient's body the tube 48 is connected to the laparoscopic cannula that has been placed partially within the bag at the location of the arm 32 and the tube 46 is attached to a laparoscopic cannula that enters directly into the peritoneal cavity. With this arrangement it is not necessary to deliver the tube assembly along with the bag into the peritoneal cavity. The tube 46 may also include a valve that when activated, simultaneously halts the flow of gas through the tube from the insufflator and vents the peritoneal cavity. The effect is an increased pressure difference between the interior of the bag and the peritoneal cavity allowing for more rapid and greater expansion of the bag.

Figure 3:
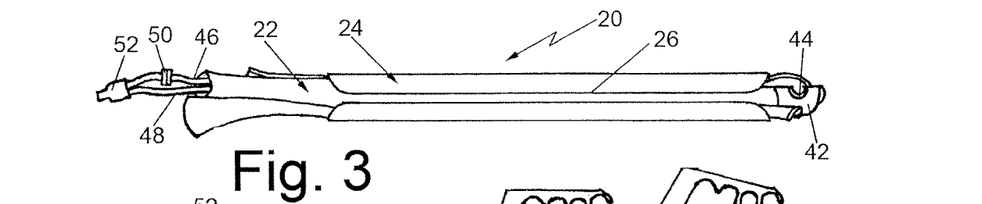
FIG. 3 is a plan view of the collection bag disposed within the introducer ready for use.
Figure 4:
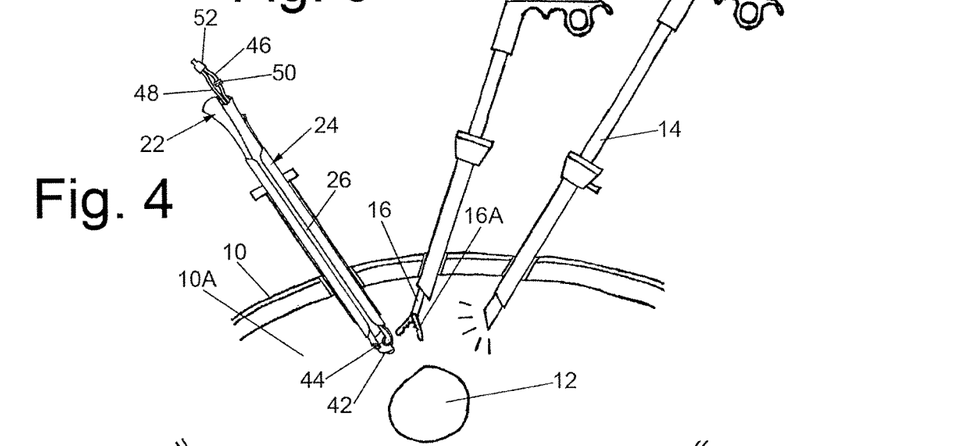
FIG. 4 is 1 is a cross-sectional view illustration of the entrapment system of this invention shown in the process of introducing the collection bag into an insufflated abdomen of a patient by means of the introducer.

Turning now to FIGS. 3-5 one exemplary method of morcellating a specimen and collecting any material that may be produced during the morcellation within the collection bag of this invention will now be described. That method basically entails folding or rolling up the specimen bag 22 so that it can be inserted through the longitudinally extending slit 26 in the introducer 24, with the distal end portion (i.e., the tab 42) of the bag extending out one end of the introducer and with the other end of the bag, i.e., the end with the Y-connector 52 of the tube assembly and the portion of the bag adjacent its mouth, extending out of the opposite end of the introducer. That configuration is shown in FIG. 3. The system 20 is now ready for deployment in the abdomen of the patient. To that end, as shown in FIG. 4, the introducer with the collection bag therein is introduced through a cannula in a port in the patient's abdominal wall 10 so that the distal end of the system 20 is located within the insufflated peritoneal cavity 10A adjacent the specimen 12 to be morcellated. In this case the specimen is shown in the form of an excised fibroid tumor, but could be any anatomic structure, e.g., an excised uterus.

The patient's abdomen had been insufflated with carbon dioxide from a conventional insufflator (not shown) via the insufflation line or conduit 68 and which is connected to an insufflation port (not shown) to the patient abdomen. A conventional laparoscope 14 or other camera or viewing instrument extends through another port into the insufflated abdomen. A conventional grasper 16 extends through another port into the insufflated abdomen. If desired, there may be more ports with instruments, e.g., graspers, extending therethrough into the insufflated abdomen.

Once the distal end of the collection bag 22 is within the insufflated peritoneal cavity, the tab 42 having the hole 44 therein is grasped by the grasping jaws 16A of the grasper 16 while being viewed on a video monitor (not shown) coupled to the laparoscope 14. The operator or user then manipulates the grasper 16 (and any other grasper that may be used and which extends through another port) to pull the collection bag 22 completely into the insufflated peritoneal cavity while holding the proximally extending portion of the introducer 24 to ensure that it isn't pulled into the insufflated peritoneal cavity.

Figure 5:
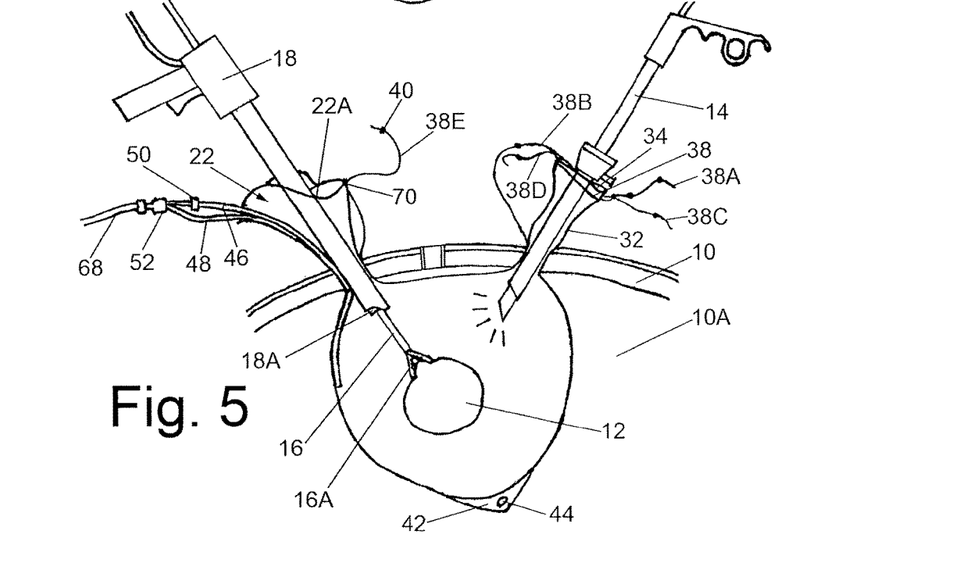
FIG. 5 is a cross-sectional view illustration, like that of FIG. 4, but showing the collection bag enclosing a specimen, with the specimen being drawn into the blade of a conventional morcellator and being imaged by a conventional laparoscope, and with the collection bag precluding any material produced by the morcellation procedure from being dispersed into the peritoneal cavity.

The introducer 24 can then be removed (i.e., withdrawn) from the cannula in the port through which it had been extended, and another grasper introduced through that port. That other grasper can be used with the grasper 16 to open the mouth 22A of the collection bag by grasping the undulating edges 30A and 30B of the bag's mouth to open the bag and then manipulating the bag so that the specimen 12 is introduced into to bag through the open mouth of the bag. This action is facilitated by observing the interior of the peritoneal cavity by means of the laparoscope 14. Once the specimen 12 is within the collection bag 22, another grasper 16 is then extended through the port so that its grasping jaws 16A are within the insufflated abdomen. Those jaws are then used to grasp the Y-connector 52 at the proximal end of the tubes 46 and 48 under visualization of the laparoscope. The grasper is then manipulated to pull the Y-connector into the cannula, removing the cannula and pulling the Y-connector through the port until the Y-connector and the mouth 22A of the collection bag is located outside the patient's abdomen. The operator or user then pulls on the undulating edge portions 30A and 30A of the bag to separate those edges and spread them apart, all the while pulling the bag in the proximal direction to provide an open entryway to the mouth of the bag. It is through this open entryway that the distal or working end of a conventional morcellator 18 is introduced and extended so that it is within the collection bag in the patient's peritoneal cavity as shown in FIG. 5.

The conduit 68 from the insufflator is then disconnected from the trocar which had been used to initially insufflate the patient's peritoneal cavity and is connected to the Y-connector 52 of the tube assembly that is now outside the patient's abdomen. As mentioned earlier the tube assembly includes the tube 48 whose apertures 64 are in fluid communication with the interior of the collection bag, and the tube 46 whose apertures 56 are in fluid communication with the exterior of the collection bag. The check valve 50 is located in the tube 46 and has a cracking pressure of a couple of mm of Hg. Accordingly, when the Y-connector 52 is connected to the conduit 68 from the insufflator, the collection bag will inflate, i.e., the internal pressure within the bag will be approximately a couple of millimeters of Hg higher than the pressure within the insufflated peritoneal cavity.

Once the collection bag is inflated, the arm 34 of the collection bag can be grasped by the jaws 16A of another grasper extending through the trocar of any suitably sized port, such as the port that the laparoscope had been extended through, whereupon that grasper can be used to pull the free end of the arm 32 out of the patient's abdomen through the associated port, removing the cannula in the process. As mentioned earlier the free end of the arm includes a mouth 34 at which a purse string closure mechanism is located. Once the free end of the arm 32 is located outside the patient's abdomen the segments 38C and 38D of the drawstring 38 are pulled outward (apart) to open the mouth 34. The distal end of a laparoscope 14, e.g., the initially used laparoscope which had been removed from the trocar, can then be introduced through the open purse string mouth 34 of the collection bag's arm 32 until it is within the inflated bag 22 so that the laparoscope can be aimed in any direction within the inflated bag. Thus, the laparoscope can be aimed at the distal or working end of the morcellator 18 and/or the specimen 12. Alternately a cannula is placed within the open purse-string mouth and the laparoscope is placed within the cannula.

Another grasper 16 can then be inserted through the central passageway of the morcellator 18 so that its jaws 16A are located within the inflated collection bag to grasp the specimen 12 and pull it toward the blade 18A of the morcellator, all the while such action can being viewed by the operator via the image on the video display coupled to the laparoscope. The action of the morcellator cuts a strip of tissue from the specimen, e.g., the strip is somewhat like the strip resulting when one uses a peeler to peel an apple. The morcellated strip extends and is pulled through the morcellator for collection outside the patient's body. Any cells, tissue, body fluids, etc., resulting from the cutting action of the morcellator on the tissue of the specimen are contained and trapped within the interior of the collection bag 22.

After the morcellation is completed, the morcellator is removed from the interior of the collection bag 22 by withdrawing it completely from the collection bag. The laparoscope 14 and cannula are also removed from the collection bag 22 by withdrawing them completely from the arm 32. The mouth 34 of the arm 32 is then closed tightly by pulling outward on the segments 38A and 38B of the closure drawstring 38. The perforations or holes 36 in the material contiguous with the mouth 34 of the arm provide some "give" to ensure that the material at the mouth of the arm collapses or gathers sufficiently to effectively seal the mouth 34 of the arm. Once this has been accomplished the operator or user can then push the extending portion of the arm 32 from outside the abdomen back through the port so that the entire arm is within the peritoneal cavity. The portion 38E of the drawstring 38, which extends through an opening in the portion of the collection bag adjacent the bag's mouth 22A ensures that the arm 32 does not fall down under the force of gravity, but is instead held upward close to the mouth 22A of the collection bag. This action ensures that if any material had gained egresses through the now closed and sealed mouth 34 of the collection bag's arm, it will not be dispersed into the peritoneal cavity.

Once the arm of the collection bag is extended through the port through which the mouth 22A of the bag 22 extends, the Y-connector 52 to the insufflator conduit 68 can be disconnected and the insufflator turned off. At that point the operator or user can grasp the top portion of the collection bag 22 contiguous with its mouth 22A while spreading it apart and pulling on it in the proximal direction until the bag is completely out of the peritoneal cavity and outside the patient's body. At this point the collection bag with its contents can be disposed of in any suitable manner.

It should be pointed out at this juncture that the shape and size of the collection bag as disclosed above is merely exemplary of various shaped and size bags envisioned by this invention. Moreover the bag may include more than one projection or arm. Further still, other means can be used to effect the selective opening and closing of the mouth of the arm(s) in lieu of the disclosed drawstring arrangement. Moreover, other means than the disclosed tube assembly can be used to ensure that the collection bag is inflated when deployed.

Figure 6:
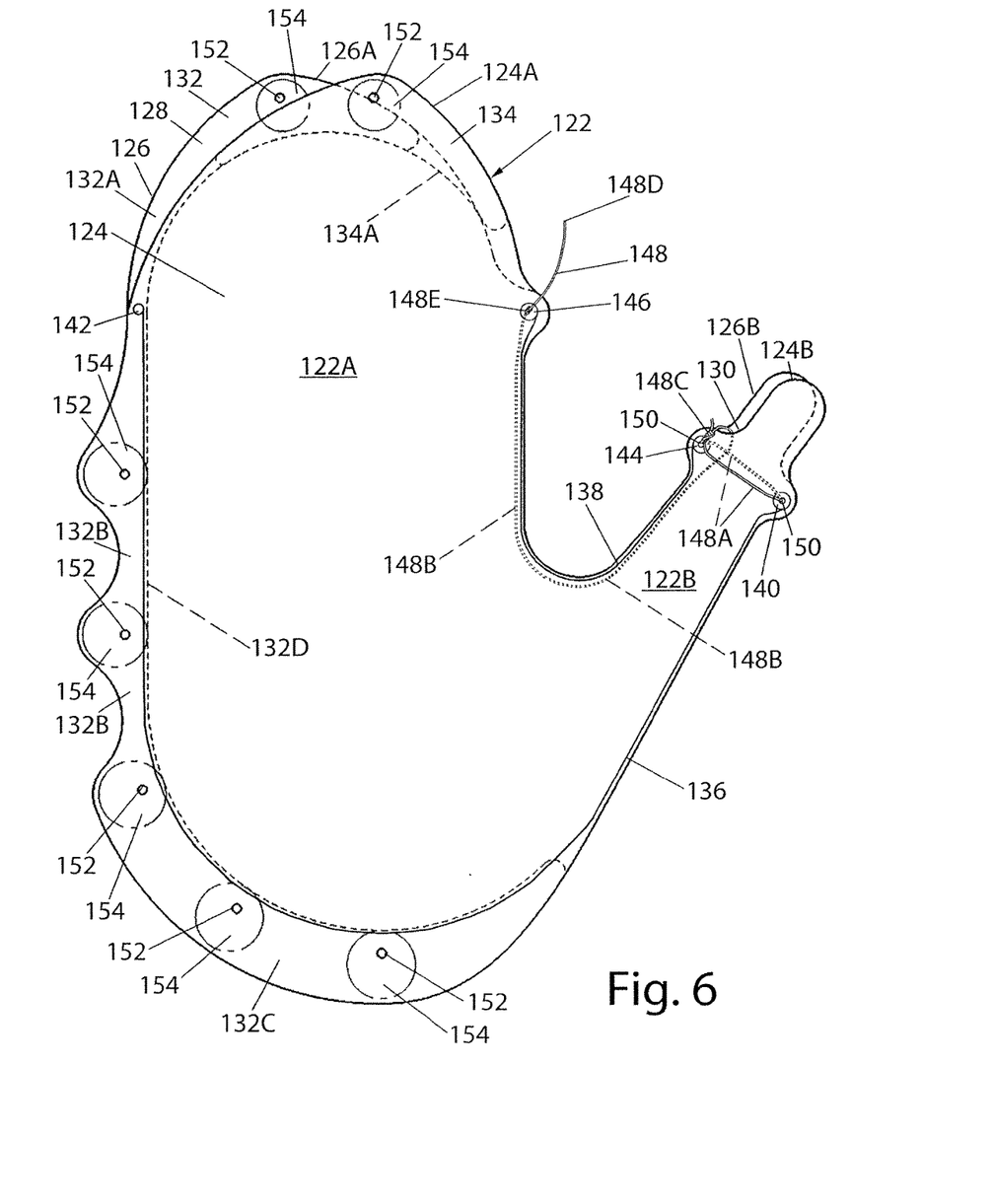
FIG. 6 is a plan view of a more preferred exemplary embodiment of a morcellation collection and entrapment bag forming one portion of a biological structure collection and entrapment system constructed in accordance with one aspect of this invention.
Figure 8:
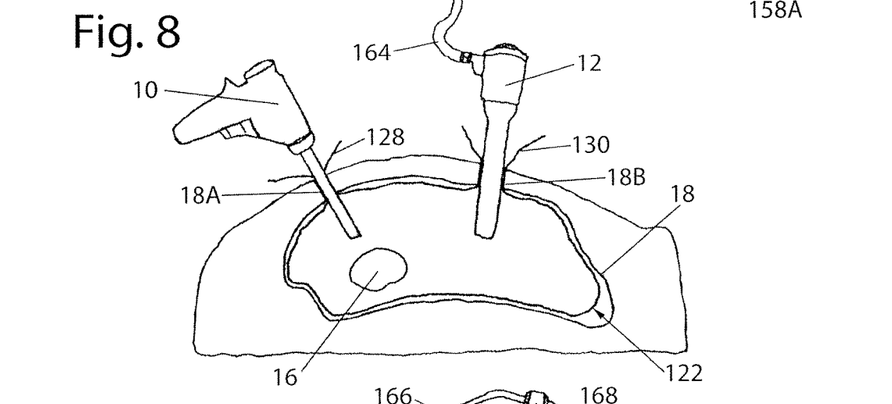
FIG. 8 is an illustration showing use of the collection and entrapment bag of FIG. 6 in use during a morcellation procedure in the peritoneal cavity of a patient.
Figure 9:
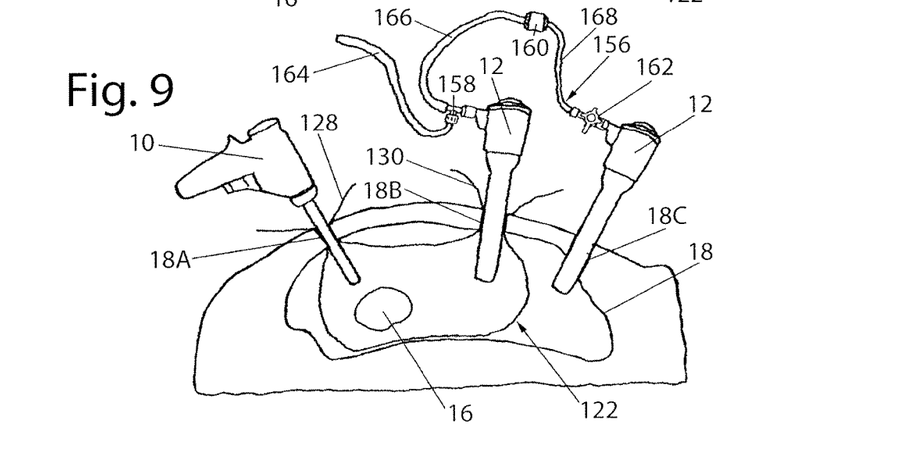
FIG. 9 is an illustration similar to FIG. 8 but showing a morcellation system constructed in accordance with this invention including the collection and entrapment bag of FIG. 1 and an insufflation tubing assembly constituting an optional portion of that system in use during a morcellation procedure in the peritoneal cavity of a patient.

Turning now to FIG. 6, a more preferred embodiment of a collection and entrapment bag 122 constructed in accordance with this invention and forming a portion of a biologic structure collection system. Two exemplary variants of the collection system are shown in FIGS. 8 and 9 for use with a conventional morcellator 10 (or some other specimen/tissue removal instrument), at least one conventional cannula 12, and a conventional laparoscope 14 (FIG. 10) to effect the removal of a specimen e.g., a fibroid tumor, organ or other biologic structure 16, from a cavity, e.g., the peritoneal space 18, of a patient during a laparoscopic procedure.

The collection bag 122 basically comprises a hollow body formed of two sheets or panels 124 and 126 of any suitable flexible material, e.g., polyurethane, of any suitable thickness, e.g., 0.07 to 0.20 mm. The sheets 124 and 126 overlie each other and together have a profile somewhat like a mitt. Portions of the sheets 124 and 126 adjacent their peripheral edges are sealed together, as will be described later, to form a hollow interior space arranged to receive the specimen 16. Being of somewhat mitt-like in shape the bag 122 includes a main section 122A and an angularly projecting finger or section 122B. The upper end portions of the two sheets 124 and 126 of the bag's main section 122A are in the form of respective tabs, and are not sealed together to form a first or primary mouth 128 of the bag. The mouth 128 is in communication with the hollow interior of the bag. In particular, the top portion of the upper sheet 124 forming section 122A is in the form of a somewhat peaked arcuate tab 124A that makes up one side of the mouth 128, while the top portion of the lower sheet 126 forming section 122A is also in the form of a somewhat peaked arcuate tab 126A that makes up the other side of the mouth 128. The peaks of the two tabs 124A and 126A are laterally off-set from each other. As such a portion of the tab 126A of the lower sheet is exposed to the left of the upper sheet tab 124A. Similarly, a portion of the tab 124A of the upper sheet is exposed to the right of the lower sheet tab 126A. The offset nature of the tabs 124A and 126A facilitates the opening of the bag, given the nature of the fact that the bag is formed of two thin sheets of material which may tend to stick together, since the tabs provide easily graspable portions of each sheet that can be selectively grasped to open the mouth 128. In particular, the off-set nature of the tabs 124A and 126A enables one to selectively grasp the tabs to readily open the mouth 128 when the bag 122 is within the cavity 18 of the patient to enable the specimen 16 to be introduced through the primary mouth 128 into the hollow interior of the bag, as will be described later. Moreover, as will be described later, the tabs 124A and 126A are reinforced to facilitate the grasping thereof.

The upper end portions of the two sheets 124 and 126 of the bag's projecting or finger section 122B are also in the form of respective tabs 124B and 126B, and are not sealed together to form a secondary mouth 130 of the bag 122. The second mouth 130 is also in communication with the hollow interior of the bag. In particular, the top portion of the upper sheet 124 is in the form of an arcuate tab 124B that makes up one side of the secondary mouth 130, while the top portion of the lower sheet 126 forming section 122B is also in the form of an arcuate tab 126B that makes up the other side of the secondary mouth 130. The peaks of the two tabs 126A and 126B are laterally off-set from each other. As such a portion of the tab 126B of the lower sheet is exposed to the left of the upper sheet tab 124B. Similarly, a portion of the tab 124B of the upper sheet is exposed to the right of the lower sheet tab 126B. This feature enables one to selectively grasp the tabs 124B and 126B to readily open the secondary mouth, when desired (as will be described later).

As mentioned above the tabs 124A and 126A are reinforced. In particular, the tab 126A is reinforced by a large generally C-shaped strip 132, and the tab 124A is reinforced by a small, generally C-shaped strip 134. Each of the strips 132 and 134 is formed of flexible sheet material, e.g., polyurethane having a thickness in the range of 0.07 to 0.20 mm. The strip 132 is fixedly secured to the inner surface of the lower sheet 126 to reinforce the tab 126A, while also reinforcing the left side edge of the sheet and the bottom edge of the sheet. To that end, the strip 132 includes three portions, namely, a top portion 132A, a side portion 132B and a bottom portion 132C. The exterior edge of the strip 132 is shaped to correspond to the exterior edge of the sheet 126. In particular, the exterior edge of the top portion 132A of the strip 132 is shaped to correspond to the shape of the exterior edge of the tab 126A. The exterior edge of the side portion 132B is shaped to correspond to the left side exterior edge of the sheet 126, while the exterior edge of the bottom portion 132C is shaped to correspond to the bottom exterior edge of the sheet 26. The inner side edge of the strip 132 is C-shaped and designated by the reference number 132D. The strip 132 may be secured to the lower sheet 126 by any suitable means, e.g., welding, an adhesive, etc. Although in the exemplary preferred embodiment shown it is welded to the sheet.

The reinforcement of the tab 124A is achieved by means of the small C-shaped strip 134. The strip 134 is formed of the same material and is of the same thickness as the strip 132. As can be seen the strip 134 only extends for the central portion of the tab 124A and includes an exterior edge that is shaped to correspond to the shape of the exterior edge of the tab 124A and an interior edge 134A that is similar in shape to the upper portion of the interior edge 132D of the strip 132. The strip 134 may be secured to the upper sheet 124 by any suitable means, e.g., welding, an adhesive, etc. Although, in the exemplary preferred embodiment shown it is welded to the sheet.

As mentioned earlier, the sheets 124 and 126 are secured together along all portions of their peripheries, other than the portions forming the mouths 128 and 130. That securement can also be achieved by any suitable means, e.g., welding, adhesives, etc. In the exemplary embodiment the sheets 124 and 126 are welded together along peripheral radio-frequency (RF) weld lines 136 and 138. Each of the weld lines 136 and 138 is relatively thin, e.g., approximately 2 mm wide. The weld line 136 terminates at one end in an enlarged, e.g., circular, weld zone 140 located adjacent one side of the secondary mouth 130 of the bag. The other end of the weld line 136 terminates in an enlarged, e.g., circular, weld zone 142 located adjacent one side of the primary mouth 128 of the bag. The weld line 138 terminates at one end in an enlarged, e.g., circular, weld zone 144 located adjacent the other side of the secondary mouth 130 of the bag. The other end of the weld line 138 terminates in an enlarged, e.g., circular, weld zone 146 located adjacent the other side of the primary mouth 128 of the bag.

The secondary mouth 130 of the bag is arranged to be selectively closed, when desired. To that end, the bag includes a drawstring 148. The drawstring includes a slidably closeable loop section 148A and a pulling section 148B. The loop section 148A is coupled to the pulling section 148B by a slip knot 148C and encircles the secondary mouth 130. In particular, the two circular weld zones 140 and 144 each include a hole 150 through which the loop section 148A extends. In particular, one half of the loop section is located on the outside of the top sheet 124 at the projecting section 122B and extends through the holes 140 in the weld zones 140 and 144 so that the other half of the loop section is located on the outside of the bottom sheet 126 at the projecting section 122B. The slip knot 148C can be located on the outside of either sheet 124 or 126, and in the embodiment shown in FIG. 6 is located on the outside of sheet 124. The pulling portion 148B of the drawstring extends through the slip knot 148C into and through the secondary mouth of the bag, through the interior of the bag 122 (as shown in FIG. 6) and out through a hole in the circular weld zone 146. Thus, the free end 148D of the pulling portion 148B is located outside of the bag adjacent the primary mouth 128 of the bag. The point at which the pulling portion 148B of the drawstring emerges from the interior of the bag at the weld zone 146 is in the form of an external knot 148E to ensure that the free end 148D of the drawstring is always outside of the bag.

In order to facilitate the grasping of portions of the bag during its use, the bag 122 includes plural "grab zones". In particular, each tab 124A and 126A includes a grab hole 152 in it closely adjacent the peak of the tab. In a similar manner a plurality of similar grab holes 152 are provided in the sheets 124 and 126 along the left side edge and along the bottom edge. Each hole 152 is reinforced by a circle RF weld zone 154 surrounding the hole and joining all of the layers of material making up the bag at the point of the grab zone. Thus, each weld zone 154 in the left side of the bag and the bottom side of the bag secures the two sheets 124 and 126 and the interposed C-shaped reinforcing member to one another.

Figure 7:
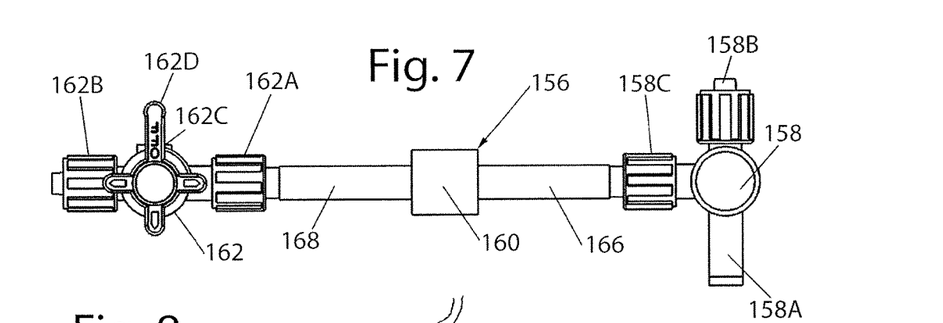
FIG. 7 is a top plan view of the optional insufflation tubing assembly for insufflating the bag of FIG. 6 in an internal cavity, e.g., the peritoneal space, within the patient.

Turning now to FIG. 7, the details of the structure of an optional tubing assembly 156 will now be discussed. The assembly 156 is arranged to be used to simultaneously expand the bag and to maintain insufflation pressure directly within the peritoneal space 18 in accordance with one aspect of this invention, which is illustrated in FIG. 9 and will be described in detail later. Suffice it for now to state that as shown in FIG. 9 the assembly 156 is configured for delivering a first pressurized gas through a first cannula 12 extending through the secondary mouth 130 into the hollow interior of the bag and for delivering a second pressurized gas through the second cannula 12 extending through a port 18C into the peritoneal cavity in the patient outside the bag. The assembly 156 includes a check valve (to be described shortly) to ensure that the pressure of the second pressurized gas is slightly less than the pressure of the first pressurized gas so that the bag is inflated within the peritoneal space.

As can be seen in FIG. 7, the tubing assembly 156 basically comprises a T-connector 158, a check valve 160 and a vented valve or stop-cock 162. The T-connector is of conventional construction and could, if desired, be a "Y-connector". In either case it includes an inlet port 158A arranged to be connected to a conduit or tube section 164 (FIG. 9) which is in turn connected to a source of insufflation gas (not shown). The T-connector includes a first outlet port 158B and a second outlet port 158C. The first outlet port 158B is arranged to be connected to a conduit or tube section forming the inlet to a cannula 12 that is extended through the secondary mouth 130 into the interior of the bag 122 as shown in FIG. 9. The second outlet port 158C is connected to one end of a tube section 166 also forming a portion of the assembly 156. The other end of the tube section 166 is connected to one side of the check valve 160. The check valve 160 is of conventional construction and has a cracking pressure of a couple of mm of Hg. The other side of the check valve 160 is connected to one end of another tube section 168 also forming a portion of the assembly 156. The other end of the tube section 168 is connected to the venting stop-cock 162.

The venting stop-cock 162 is of conventional construction and includes an inlet port 162A to which the tubing section 168 is connected, a first outlet port 162B and a second outlet port 162C. As can be seen in FIG. 9, the first outlet port 162B is arranged to be connected to the inlet to another cannula 12 that is extended through a port 18C into the peritoneal space 18 of the patient. The other outlet port 162C is in communication with the ambient atmosphere. The venting stop-cock includes a handle 162D which is arranged to be rotated between a closed or "On" position and an vent or "Off" position, and vice versa. When the handle 162D is in the "On" position insufflation gas is provided from the conduit 164, through the T-connector 158, the conduit 166, the check valve 160, and the conduit 168 to the inlet to the cannula 12 that is in communication with the peritoneal space 18 to insufflate that space. When the handle 162D is moved to the "Off" or vent position, the flow of the insufflation gas is cut off and insufflation gas that had been in the peritoneal space vent to the ambient atmosphere via the cannula 18 extending through the port 18C and the now open stop-cock 162.

As mentioned earlier the optional tubing assembly 156 is configured to be used to simultaneously expand the bag 122 and maintain insufflation pressure directly within the peritoneal space 18. As will be appreciated by those skilled in the art, maintaining the bag in an expanded state facilitates morcellation by permitting visualization within the bag via a laparoscope and by keeping the sides of the bag in an outward position so that morcellation can be accomplished without risk of the morcellator cutting portion contacting and cutting the bag. Using a laparoscopic insufflator to expand the bag within the peritoneal space ensures that only safe levels of pressure are applied to the peritoneal cavity.

Figure 10:
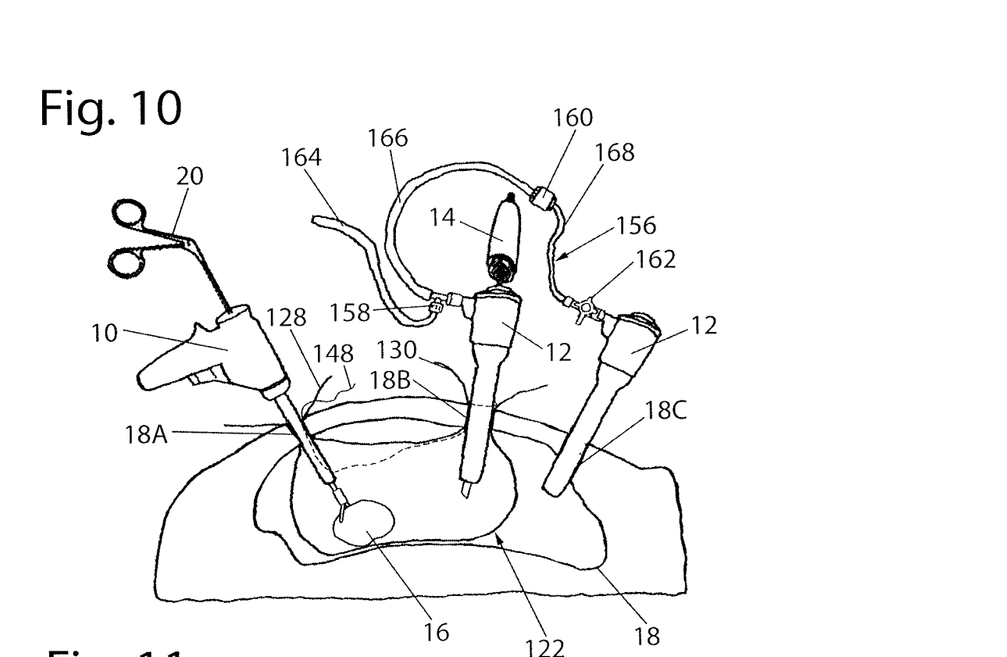
FIG. 10 is an illustration similar to FIG. 9 but showing a later step in the morcellation procedure shown in FIG. 3.
Figure 11:
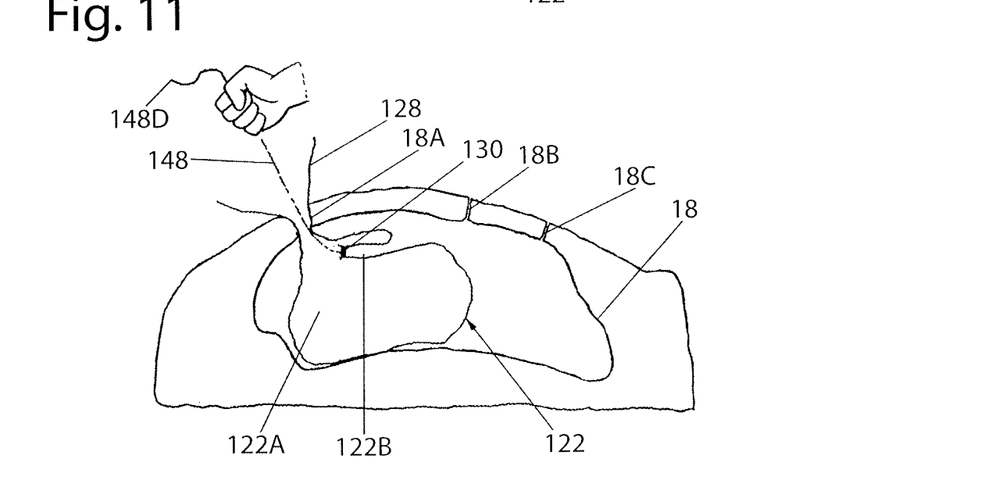
FIG. 11 is an illustration similar to FIGS. 9 and 10 but showing a still later step in the morcellation procedure shown in FIGS. 9 and 10.

Two exemplary specific methods of morcellating a resected specimen within the peritoneal space in a patient and collecting any material that may be produced during the morcellation within the collection bag of this invention will now be described. Those two methods are similar, except that one method entails the insufflation of the bag 122 within a previously insufflated peritoneal space 18 in a patient, while the other method entails the simultaneous insufflation of the bag 122 within the peritoneal space 18 and the insufflation of the peritoneal space itself. The former method is illustrated in FIG. 8, and is achieved without the use of the optional tubing assembly 156, while the latter method is illustrated in FIGS. 9-11 and is achieved by use of that optional tubing assembly. In either case the patient's peritoneal space 18 is first insufflated via a port and a laparoscope is extended through a cannula into that space to enable the visualization of the procedure. If desired, there may be more ports with instruments, e.g., graspers, extending therethrough into the insufflated peritoneal space. When the peritoneal space is sufficiently insufflated, the collection bag 122 of this invention can be folded, rolled or otherwise compacted so that it can be introduced via a patient port site, e.g., an incision, 18A in the patient's abdomen. The surgeon can then engage the last grab loop 152 of the bag 122 with a grasper, remove the cannula 12 from the patient port site to pull or insert the bag directly into the patient's peritoneal space while maintaining direct visualization. Care should be taken to ensure the port site incision is not oversized for a 15 mm cannula. The surgeon can engage additional grab loops, as necessary, to fully advance the bag into the peritoneal space. Once that has been accomplished a conventional cannula is extended through the patient port site 18A to ensure that the insufflation gas cannot escape through it.

After the bag is fully within the insufflated peritoneal space one or more conventional grasper instruments (not shown) can be inserted through any other cannula into the insufflated peritoneal space to grasp the bag by a desired one of its grasper or grab loops 152 to move the bag so that its primary mouth 128 is located adjacent the resected specimen 16 to be removed. As should be appreciated by those skilled in the art, the use of the grasper or grab loops 152 have utility not only for insertion of the bag in the peritoneal space but also for laying out, arranging, and otherwise adjusting the bag inside that space, as needed. After the bag is in the desired position vis-a-vis the specimen 16, whichever one of the tabs 124A and 126A at the bag's primary mouth 128 that is facing upward can then be folded back by a grasper to open the mouth so that the specimen can be placed or rolled onto a "placement area" in the open mouth created by the laid out tabs. The bag and/or the specimen can then be moved by the grasper(s) so that the specimen is within the hollow interior of the main section of the bag. For example, the surgeon can grasp both tabs 124A and 126A with one grasper and advance the specimen towards the bottom of the bag with a second grasper. Once that has been accomplished the portion of the tabs 124A and 126A are pulled through the port 18A after removal of the cannula therefrom. The tabs 124B and 126B forming the secondary mouth 130 are similarly pulled through another incision or port 18B that is in communication with the insufflated peritoneal space and from which a cannula had been removed. After the primary mouth 128 of the bag 122 has been extended out through the port 18A and the secondary mouth 130 has been extended out through the port 18B, the bag 122 is inflated. This can be accomplished as shown in FIG. 8 without the use of the optional tubing assembly 156, or can be accomplished as shown in FIG. 9 by use of that tubing assembly.

With respect to the method illustrated in FIG. 8, a conventional cannula 12 to which an insufflator has been connected, is introduced into the bag through the secondary mouth 130. This process can be viewed via a laparoscope extending through another cannula into the peritoneal space 18. With respect to the method illustrated in FIG. 9 a conventional cannula 12 to which the outlet 158B of the T-connector 158 of the tube assembly is connected is introduced into the bag through the secondary mouth 130. This process can be viewed via a laparoscope extending through another cannula into the peritoneal space 18. A second conventional cannula 12 to which the outlet of the venting stop-cock 162 is connected is introduced into the peritoneal space via another incision or port 18C. The operation of the check valve insures that the gas pressure delivered by the cannula extending into the bag 122 is a few mm of Hg higher than the gas pressure within the peritoneal space as delivered by the cannula extending into that space. This ensures that the bag is inflated within the peritoneal space and simultaneously insufflates the peritoneal space. If desired, the inflation of the bag within the peritoneal space can be sped up or otherwise expedited by moving the handle of the stop-cock to the "Off" or vent position, whereupon the flow of insufflating gas to the peritoneal space will be halted by the stop-cock and at the same time gas within that space will vent the ambient atmosphere through the stop-cock. This action causes the bag to inflate more quickly due to the higher differential pressure inside the bag as compared to outside the bag. Once the bag has been inflated the handle 162D of the stop-cock can be moved to the "On" position, whereupon the flow of the pressurized insufflation gas will again be delivered through the cannula 12 extending through port 18C into the peritoneal space.

After the inflation of the bag 122 and the peritoneal space has been accomplished, the resected specimen 16 is ready to be removed, e.g., morcellated. To that end, a conventional morcellator 10 can be introduced through the primary mouth 128 of the bag in port 18A and a conventional cannula with a laparoscope 14 extending therethrough can be introduced through the secondary mouth 130 of the bag in port 18B, if it is not already there. The offset nature of the tabs 124B and 126B at the secondary mouth 130 enable a surgeon or other operating personnel to readily open the secondary mouth 130 so that the cannula can be inserted therethrough even though the person's hands are gloved.

With a laparoscope extending through the secondary mouth 130 in the port 18B an unobstructed image of the interior of the bag 122 is provided to facilitate the effective and safe morcellation of the specimen 16 within the bag. To that end, a conventional grasper 20 can be inserted through the central passageway of the morcellator 10 so that its jaws are located within the inflated collection bag to grasp the specimen 16 and pull it toward the blade of the morcellator, all the while such action can being viewed on a video display coupled to the laparoscope 14 that is located within the bag. The action of the morcellator cuts a strip of tissue from the specimen, e.g., the strip is somewhat like the strip resulting when one uses a peeler to peel an apple. The morcellated strip extends and is pulled through the morcellator for collection outside the patient's body. Any cells, tissue, body fluids, etc., resulting from the cutting action of the morcellator on the tissue of the specimen is contained and trapped within the interior of the collection bag 122.

In the interest of safety the surgeon (or whichever person is effecting the procedure) should take care to ensure that the cutting portion of the morcellator or any other cutting instrument does not contact the bag material as it may cut the bag. In addition care should be taken to avoid grabbing or poking the sides of the bag with sharp instruments. Once morcellation has begun if any morcellated tissue has contacted the externalized portions of the bag due to external splatter etc., such portions should be wiped down if there is a need to advance the externalized portions back into the peritoneal space.

Figure 12:
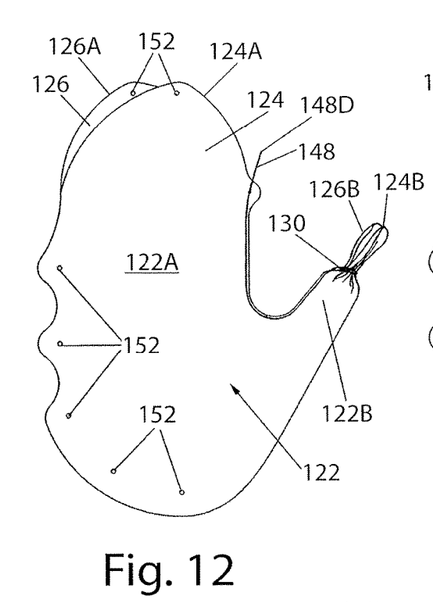
FIG. 12 is a reduced plan view showing a collection and entrapment bag, like shown in FIG. 6 during one step of its use.
Figure 13:
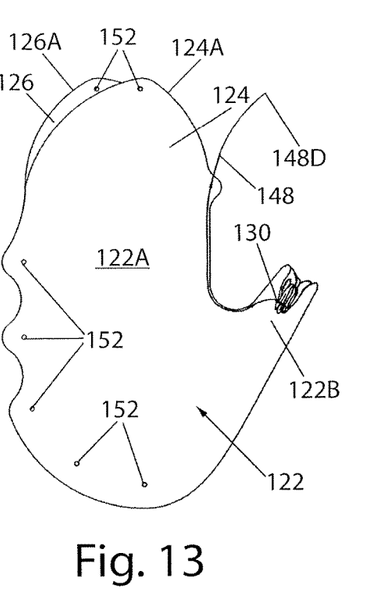
FIG. 13 is a plan view, similar to FIG. 12, but showing the collection and entrapment bag at a later step in its use.
Figure 14:
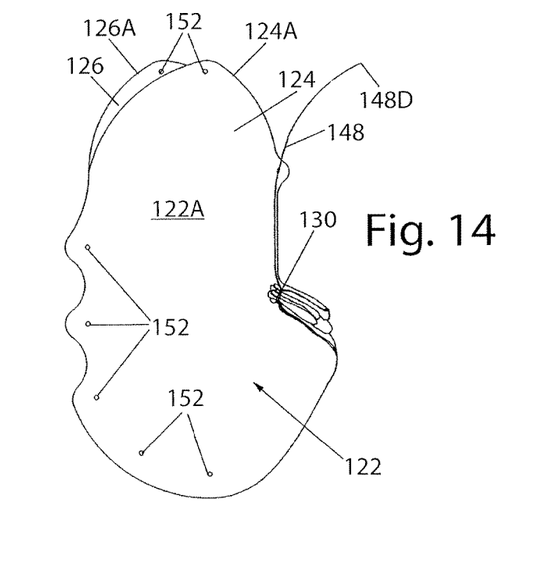
FIG. 14 is a plan view, similar to FIGS. 12 and 13, but showing the morcellation collection and entrapment bag at a still later step in its use.

After the morcellation is completed, the morcellator 10 is removed from the interior of the collection bag 122 by withdrawing it completely from the collection bag. The laparoscope 14 is also removed from the collection bag by withdrawing it completely from the secondary mouth 130. The secondary mouth 130 is then closed tightly by pulling outward on the free end 148D of the drawstring 148 to cause the loop section 148A to collapse the portion of the secondary mouth 130 within its confines to thereby seal the mouth, like shown in FIG. 12. Further pulling on the free end of the drawstring inverts the closed free end portion of the section 122B like shown in FIG. 13. This inversion of the section 122B, and its path through the inside of the bag causes a more secure seal of the secondary mouth 130, further preventing accidental spillage, or rubbing off of biologic components from the morcellation activities onto surrounding tissues. Further pulling of the free end of the drawstring brings the closed free end portion of the section 122B within the hollow interior of the section 122A, like shown in FIGS. 11 and 14. This further secures the closure of the secondary mouth 130 and prevents any escape of potentially hazardous materials from inside the bag. Continued pulling on the drawstring will eventually bring the closed end of section 122B through the primary mouth 128 and out of the patient. At that point the surgeon can grasp the tabs 124A and 126A at the top portion of the collection bag 122 while spreading those tabs apart and pulling on them in the proximal direction and also simultaneously pulling on the closed end of the section 122B until the bag is completely out of the peritoneal cavity and outside the patient's body. Care should be taken during this process to avoid applying excessive force to the bag. If needed, the port site 18A may be carefully enlarged to facilitate removal of the bag. Once the bag is fully out of the patient, it and its contents can be disposed of in any suitable manner, e.g., disposed as standard medical waste.

As should be appreciated by those skilled in the art the location of the drawstring 148 along the upper edges of the projecting section 122B and the main section 122A ensures that the section 122B does not fall down under the force of gravity during its retraction. Rather, it is held upward close to the primary mouth 128 of the collection bag during the bag's retraction from the patient. Thus, if any biologic material had gained egress through the now closed and sealed secondary mouth 130, it will not be dispersed into the peritoneal cavity. The use of the off-set tabs 124B and 126B on the secondary mouth 130 aid in opening the second mouth with gloved hands. In addition, they aid in the introduction of the cannula and laparoscope through the mouth 130 for visualization the inside of the bag. The tabs 124B and 126B also seem to help in preventing leakage when the secondary mouth 130 is closed and inverted within the body of the bag, causing the offset tabs to further fold up and block any potential opening in the drawstring closure of the secondary mouth. Having the neck portions of the mouths 128 and 130 lining the port sites 18A and 18B, respectively, protects them from potential exposure to morcellated materials. It also enables the sealing of the bag for insufflation, and effective containment of morcellated biological materials. Inasmuch as the top edges of the tabs 124A and 126A are reinforced with extra material, they enable the bag to be held open by lifting the bag from a single point, marked by the hole 152 in each tab. This facilitates easier loading of the specimen into the bag as the top tab can be easily lifted and pulled over the specimen, and grabbed concurrently with the bottom tab. At that point both tabs could be lifted, via the grab loop in the top of each tab, causing the specimen to roll or slide into the bag via gravity, with a little help, if needed, from an assisting grasper to push the specimen deeper into the body of the bag. Once the specimen is loaded into the bag, the grab loops in the top of each tab can be used to pull the primary mouth 128 of the bag up through the port site 18A that will be used by the morcellator.

It should be pointed out at this juncture that the shape, size and features of the collection bag as disclosed above are merely exemplary of various collection bags envisioned by this invention. Moreover such bags may include more than one projecting section. Further still, other means can be used to achieve the selective opening and closing of the secondary mouth of the projecting section(s) in lieu of the disclosed drawstring arrangement. Moreover, other means than the disclosed tube assembly can be used to ensure that the collection bag is inflated when deployed. In accordance with one exemplary commercial embodiment of this invention the bag and the optional tubing assembly can be provided in a sterile, e.g., Tyvek-PET/PE peel pouch, (not shown) for single patient use, but other arrangements for providing the system of this invention are contemplated. Moreover, any collection bag constructed in accordance with this invention can be used in various ways during laparoscopic surgery. For example, the bag can be placed within the peritoneal space via a patient port site. A tumor, organ or any other biologic structure that is to be removed from the patient and which has been resected can then be placed within the bag for isolation and removal from the patient. For biologic structures/specimens small enough to be removed directly via an incision, the bag can be removed from the patient with the biologic structure/specimen contained within the bag. For larger biologic structures/specimens, it can be morcellated under direct visualization, within the bag in the peritoneal space, and in a contained manner, by placement of a morcellator into the bag's primary (first) mouth and placement of a laparoscope into the bag's secondary (second) mouth, via a laparoscopic cannula. The bag can then be expanded by applying a conventional insufflating gas from a laparoscopic insufflator, via the laparoscopic cannula, into the bag, creating an expanded, isolated volume where the biologic structures/specimen can be visualized and morcellated without spread of the tissue remnants throughout the peritoneal space.

Without further elaboration the foregoing will so fully illustrate our invention that others may, by applying current or future knowledge, adopt the same for use under various conditions of service.

We claim:

1. A collection bag for use in a procedure on a biologic structure in a cavity in a patient to entrap biologic material produced by the procedure, said bag being configured to be introduced through a port into the patient and comprising a body formed of a flexible sheet material, said body having a hollow interior, a top portion including a first mouth located thereat and a second portion projecting outward from said top portion, said second portion having a second mouth thereat, said first mouth being openable to enable the biologic structure to be introduced therethrough into said hollow interior and to enable an instrument to be introduced therethrough to engage the biologic structure to effect a procedure on the biologic structure, said second mouth being openable to enable a viewing instrument to be extended therethrough into said hollow interior to enable the visualization of the engagement of the biologic structure by the instrument, said second mouth comprising a closure and a first portion of a draw-string coupled to said closure, said closure being initially open to enable the viewing instrument to be inserted through said second mouth and removed from said second mouth, said first portion of said draw-string being configured to be pulled to close said closure after the viewing instrument has been removed from said second mouth to thereby entrap the biologic material produced by the procedure within said hollow interior, whereupon said collection bag may be withdrawn from the body of the patient through the port.

2. The collection bag of claim 1 wherein said closure comprises a second portion of said draw-string, said second portion of said draw-string being extendable through the port to draw said second portion of said collection bag toward said port when said closure is closed, whereupon said collection bag can be withdrawn from the body of the patient through the port.

3. The collection bag of claim 1 wherein the port comprises a first port and wherein said first mouth comprises a pair of projecting edges, one of said pair of projecting edges of said first mouth comprising a first edge portion of said first mouth and the other of said pair of projecting edges of said first mouth comprising a second edge portion of said first mouth, said second edge portion of said first mouth being laterally off-set from said first edge portion of said first mouth, said first mouth being openable by grasping at least one of said pair of tabs of said first mouth to enable the biologic structure to be introduced therethrough into said hollow interior and to enable an instrument to be introduced therethrough to engage the biologic structure, said second mouth being configured for disposition within a second port into the patient and openable to enable a viewing instrument to be extended therethrough into said hollow interior to enable the visualization of the biologic structure.

4. The collection bag of claim 3 wherein said collection bag is formed by a pair of panels of flexible material, one of said panels having a top edge portion forming one of said pair of projecting edges of said first mouth and the other of said pair of panels having a top edge portion forming the other of said pair of projecting edges of said first mouth.

5. The collection bag of claim 3 wherein said body comprises a main section and a projecting section, said projecting section projecting away from said main section, said main section having a top portion at which said first mouth is located, said projecting section having a top portion at which said second mouth is located.

6. The collection bag of claim 5 wherein said body is of a generally mitt-like shape.

7. The collection bag of claim 3 additionally comprising a drawstring coupled to said second mouth of said collection bag, said drawstring being configured to close said second mouth and draw said second mouth into said hollow interior, whereupon said collection bag can be removed from the patient through the first port.

8. The collection bag of claim 3 wherein said collection bag is formed of a polymer material.

9. The collection bag of claim 8 wherein said polymer material comprises polyurethane.

10. The collection bag of claim 3 wherein said collection bag forms a part of a system, said system additionally comprising a tubing assembly.

11. The system of claim 10 wherein said tubing assembly is configured for delivering a first pressurized gas through a first conduit into the hollow interior of the collection bag and for delivering a second pressurized gas through a second conduit into the cavity in the patient and outside of the collection bag, with the pressure of the second pressurized gas being slightly less than the pressure of the first pressurized gas so that the collection bag is inflated within the cavity of the patient.

12. The system of claim 11 wherein said tubing assembly additionally comprises a differential pressure control valve for ensuring that the pressure of the second pressurized gas is slightly less than the pressure of the first pressurized gas.

* * * * *